(12) United States Patent
Xu et al.

(10) Patent No.: US 11,576,947 B2
(45) Date of Patent: Feb. 14, 2023

(54) ORAL COMPOSITION AND METHOD

(71) Applicants: Kunming Lanchie Dental Hospital, LTD, Kunming (CN); Kunming Yeshui Bio-Tech, LTD, Kunming (CN)

(72) Inventors: Yun Xu, Kunming (CN); Lei Zhang, Kunming (CN); Yang Song, Kunming (CN); Kewang Lu, Dover, DE (US)

(73) Assignees: Kunming Lanchie Dental Hospital, LTD., Kunming (CN); Kunming Yeshal Bio-Tech, LTD., Kunming (CN)

( * ) Notice: Subject to any disclaimer, the term of this patent is extended or adjusted under 35 U.S.C. 154(b) by 0 days.

(21) Appl. No.: 16/422,467

(22) Filed: May 24, 2019

(65) Prior Publication Data
US 2020/0306344 A1 Oct. 1, 2020

(51) Int. Cl.
*A61K 8/22* (2006.01)
*A61K 38/17* (2006.01)
*A61K 8/81* (2006.01)
*A61K 33/40* (2006.01)
*A61Q 11/00* (2006.01)

(52) U.S. Cl.
CPC .......... *A61K 38/1729* (2013.01); *A61K 8/22* (2013.01); *A61K 8/8176* (2013.01); *A61K 33/40* (2013.01); *A61Q 11/00* (2013.01)

(58) Field of Classification Search
CPC ........ A61K 8/22; A61K 8/8176; A61K 33/40; A61K 38/1729; A61Q 11/00
See application file for complete search history.

(56) References Cited

U.S. PATENT DOCUMENTS

| | | | |
|---|---|---|---|
| 2005/0031553 A1* | 2/2005 | Mori | A61K 8/38 424/53 |
| 2006/0024246 A1* | 2/2006 | Maitra | A61K 8/8176 424/49 |
| 2008/0261844 A1* | 10/2008 | Ruppert | A61Q 19/10 510/158 |
| 2011/0135584 A1* | 6/2011 | Mallard | A61K 47/32 424/59 |
| 2012/0289575 A1* | 11/2012 | Lu | A61K 31/4015 514/423 |

FOREIGN PATENT DOCUMENTS

| | | | | |
|---|---|---|---|---|
| DE | 202004014421 U1 * | 3/2005 | | A61C 19/063 |
| WO | WO-2016153144 A1 * | 9/2016 | | A61K 8/81 |

OTHER PUBLICATIONS

Paulson, DS, Handbook of Topical Antimicrobials, Ch5, (2003), pp. 99-116, CRC Press, Boca Raton, FL.
Stanga, M, Sanitation: Cleaning and Disinfection in the Food Industry, Ch10, (2010), pp. 375-385, Wiley-VCH Verlag GmbH & Co. KGaA, Weinheim, Germany.

* cited by examiner

*Primary Examiner* — Ali Soroush
(74) *Attorney, Agent, or Firm* — Mendelson IP; Elliot C. Mendelson

(57) ABSTRACT

The present invention relates to oral composition and the method of preparation and use of such composition for inhibiting, reducing, and/or disrupting oral biofilm. The composition comprises a stabilizing matrix, a cationic biocide, and a peroxide source.

20 Claims, No Drawings

ORAL COMPOSITION AND METHOD

BACKGROUND OF THE INVENTION

Biofilm is a collection of micro colonies with water channels in between and an assortment of cells and extra cellular glycoproteins, polysaccharides and proteins, nucleic acids, or combinations of these macromolecules, and which protects the inhabiting organisms from antiseptics, antibiotics, and host cells.

In the oral environment, biofilms form when bacteria adhere to surfaces in the oral cavity and begin to excrete a slimy, glue-like substance that can adhere to all kinds of substrates found in the oral environment, including biological tissues (gingival tissues and oral mucosa tissues), enamel, dentin, cementum, restoratives, metals, alloys, composites, plastics, porcelains, medical implant materials and devices of prosthodontics and orthodontics.

Biofilms in the oral environment contain communities of disease-causing bacteria and their uncontrolled accumulation has been associated with oral diseases, caries and periodontal diseases (both gingivitis and periodontitis). An established oral biofilm can be very difficult to disrupt, whether by mechanical or chemical means.

The biofilm matrix may provide protection to biofilm-forming bacteria from biocides. It has been well documented that antimicrobials have difficulty penetrating the biofilm's surface layer and because of that, they are less effective on bacteria in an established biofilm, as compared to planktonic bacteria. It has been estimated, for example, that bacteria within biofilms are upwards of 1,000-fold more resistant to conventional antibiotics (Rasmussen et al., Int. J. Med. Microbiol., 2006, 296: 149). As a result, antimicrobial agents (such as antibiotics or antiseptics) are generally not very effective in killing or inhibiting the microorganisms that are deeply embedded within the biofilm. For similar reasons, herbal extracts and essential oils also have very low efficacy against biofilms.

In other contexts, strong antimicrobials have been used to kill bacteria in a biofilm, such as Bisguanide, halogenated diphenyl ether (e.g. triclosan); halogenated quaternary ammonium compounds (e.g., hexadecylpyridinium chloride, benzalkonium chloride, tetradecylpyridinium chloride, N-tetradecyl-4-ethylpyridinium chloride); halogen compounds (e.g., elemental halogens, halogen oxides (e.g., NaOCl, HOCl, HOBr, $ClO_2$); interhalides (e.g., iodine monochloride, iodine dichloride, iodine trichloride, iodine tetrachloride, bromine chloride, iodine monobromide, or iodine dibromide); polyhalides, hypochlorite salts, hypochlorous acid, and hypobromite salts. Generally, these materials are effective in preventing the unwanted growth of microorganisms. But, most of these compounds are not suitable to be used in oral cavity due to the toxicities and irritations to human body and oral tissues. Bisguanide antiseptics have a bitter taste and stain tooth surfaces, making it unpleasant to users. Triclosan is a potential mutagen, may cause hormone imbalances, and may harm the immune system. Trislocan may also increase the calcium levels inside neurons and with this, theoretically, affect mental development.

Therefore, a high efficacy biocide without unwanted side effects is in need for dental care.

Peroxides are known to be useful for cleaning and whitening teeth, as well as killing cariogenic bacteria. However, peroxide compounds are highly reactive and can spontaneously decompose. Some known dentifrice compositions that include peroxide may exhibit an unacceptable level of peroxide decomposition and loss of efficacy as a result of being stored prior to sale or use. Moreover, peroxide is not compatible with many commonly used ingredients in toothpaste. Consequently, it has been difficult to formulate a stable peroxide containing toothpaste.

Therefore, there is an ongoing and unmet need for an effective composition for oral care, which combines a high efficacy biocide without unwanted side effects and peroxide for effective biofilm removal through the synergistic effect of a cationic biocide and peroxide. The embodiments of the present invention aim to meet these needs.

BRIEF SUMMARY OF THE INVENTION

The present invention provides a composition, which comprises a stabilizing matrix, a peroxide source, and a cationic biocide for inhibiting, reducing, and/or disrupting oral biofilm.

The composition of invention provides an oral care composition comprising (i) stabilizing matrix, (ii) a cationic biocide, and (iii) a peroxide source.

The present invention also provides a composition according to the above, having a stabilizing matrix that helps keep peroxide and cationic biocide stable in a single-phase paste, which is capable for long-term storage and is suitable for everyday consumer use.

The present invention also provides a composition according to any of the above, where the stabilizing matrix of the composition maintains the efficacy of active ingredient, cationic biocide, and at the same time to stabilizes the peroxide source in the composition.

The present invention also provides a composition according to any of the above, where the stabilizing matrix comprises of a carrying agent, a thickening system and some compatible adjuvants.

The present invention also provides a composition according to any of the above, where the carrying agent of the matrix comprises a polyhydric alcohol. In some embodiments, the polyhydric alcohol may be propylene glycol.

The present invention also provides a composition according to any of the above, where the propylene glycol is present in amounts ranging from 75% to 85%, based on the matrix weight of the composition.

The present invention also provides a composition according to any of the above, where the stabilizing matrix comprises a thickening system. In some embodiments, the thickening system of the stabilizing matrix comprises polyvinylpyrrolidone and silicone dioxide.

The present invention also provides a composition according to any of the above, where polyvinvlpyrrolidone may be present in amounts ranging from 2% to 6%, based on the matrix weight of the composition.

The present invention also provides a composition according to any of the above, where the thickening system of the stabilizing matrix comprises a silicone dioxide. In some embodiment, the silicone dioxide may be fumed silicone dioxide. In some embodiments, the fumed silicone dioxide may be hydrophilic fumed silicone dioxide.

The present invention also provides a composition according to any of the above, where hydrophilic fumed silica may be present in amounts ranging from 6% to 11%, based on the matrix weight of the composition. In some embodiments, the hydrophilic fumed silicone dioxide may be pharmaceutical grade.

The present invention also provides a composition according to any of the above, where the compositions of the invention optionally comprise an anti-caries agent. In some embodiments, the invention may optionally include an effective amount of fluoride, or a fluoride ion source. In certain embodiments, a fluoride ion may be present in amounts ranging from 0.05% to 0.15%, based on the weight of the composition.

The present invention also provides a composition according to any of the above, where the stabilizing matrix of the composition of present invention optionally comprises adjuvants that are compatible with each other and compatible with the cationic biocide and peroxide source in the system. In some embodiments, adjuvants may include one or more foaming agents, one or more flavorings, one or more coloring agents, one or more chelating agents, one or more antioxidants, and the like.

The present invention also provides a composition according to any of the above, where the peroxide source of the composition may be selected from hydrogen peroxide, carbamide peroxide, calcium peroxide, percarbonates, perborates, and cross-linked polyvinylpyrrolidone complexed with hydrogen peroxide. In some embodiments, the peroxide source is present in amounts ranging from 0.1% to 2.0%, optionally from 0.1% to 1.0%, optionally from 0.8% to 1.2%, based on calculated hydrogen peroxide weight of the composition.

The present invention also provides a composition according to any of the above, where the cationic biocide of the composition is selected from group consisting of dual chain quaternary ammonium biocide and a single chain quaternary ammonium biocide. In some such embodiments, the cationic biocide may be PODA: Proline, 5-oxo-, ion(1-), N-decyl-N,N-dimethyl-1-decanaminium (1:1). In some such embodiments, the cationic biocide may be Hexadecylpyridinium chloride. In some embodiments, the cationic biocide may be present in amounts ranging from 0.05% to 1.0%, optionally from 0.05% to 0.2%, optionally from 0.05% to 0.1%, based on the weight of the composition.

The present invention also provides a composition, according to any of the above, that provides a single phase oral care composition that not only inhibits, reduces, and/or disrupts the biofilm of oral cavities, but it also is stable for long-term storage and is suitable for everyday consumer use.

By applying the composition to oral cavity in inhibition, reduction, and disruption biofilm, the compositions of the present invention can promote or improve oral health and/or systemic health, including cardiovascular health. e.g., by reducing potentials for systemic effects of inflammation from periodontal disease The present invention also provides a composition according to any of the above, comprising (i) about 0.05% to about 0.2% of a cationic biocide selected from the group consisting of a dual chain quaternary ammonium biocide and a single chain quaternary ammonium biocide, (ii) about 0.1% to about 2.0% of a compatible peroxide source, and (iii) about 85% to about 99% of a stabilizing matrix, where the percentages are based on the weight of the composition and the percent of the peroxide source is calculated as a weight percent equivalent as if the peroxide source were hydrogen peroxide.

The present invention also provides a composition according to any of the above, where the stabilizing matrix comprises a carrier, a thickening system, and optionally further includes one or more compatible adjuvants.

The present invention also provides a composition according to any of the above, where the carrier is polyhydric alcohol. In some embodiments, the polyhydric alcohol is propylene glycol and is present in amounts of about 40% to about 90%, where the percentages are based on the weight of the composition. In some embodiments, the composition may have about 75% to about 85% propylene glycol.

The present invention also provides a composition according to any of the above, where the thickening system comprises polyvinyl pyrrolidone. In some embodiments, the composition may comprise about 2% to about 6% polyvinyl pyrrolidone, where the percentages are based on the weight of the composition.

The present invention also provides a composition according to any of the above, where the thickening system comprises fumed silica. In some such embodiments, the fumed silica is hydrophilic fumed silica and may be present in amounts of about 5% to about 11%, where the percentages are based on the weight of the composition.

The present invention also provides a composition according to any of the above, where the peroxide source is carbamide peroxide.

The present invention also provides a composition according to any of the above, where the cationic biocide is proline, 5-oxo-, ion(1-), N-decyl-N,N-dimethyl-1-decanaminium (PODA).

The present invention also provides a composition according to any of the above, where the cationic biocide is hexadecylpyridinium chloride.

The present invention also provides a composition according to any of the above, where the cationic biocide is proline, 5-oxo-, ion(1-), N-decyl-N,N-dimethyl-1-decanaminium, the peroxide source is carbamide peroxide, and the thickening system comprises propylene glycol, polyvinylpyrrolidone, and hydrophilic fumed $SiO_2$.

The present invention also provides a composition according to any of the above, where the cationic biocide is hexadecylpyridinium chloride, the peroxide source is carbamide peroxide, and the thickening system comprises propylene glycol, polyvinylpyrrolidone, and hydrophilic fumed $SiO_2$.

The present invention also provides a composition according to any of the above, where the thickening system comprises a compatible foaming agent selected from the group consisting of poloxamer or fatty acid polyoxyethylene ether. In some such embodiments, the compatible foaming agent may be poloxamer 188. In some such embodiments, the compatible foaming agent may be fatty alcohol polyoxyethylene ether 9.

The present invention also provides a composition according to any of the above, where the composition is substantially free of added water.

The present invention also provides a composition according to any of the above, where the composition is shelf stable for at least 6 months. In some such embodiments, the composition may also be shelf stable for at least 1 year.

The present invention also provides a composition according to any of the above, having an MIC of less than 0.0025 mg/mL against *Streptococcus mutans* ATCC 25175, *Actinobacillus viscosus* ATCC 15987, and/or *Bacteriodes fragilis* ATCC 25285.

The present invention also provides a composition according to any of the above, having an MIC of less than 0.00125 mg/mL against *Streptococcus mutans* ATCC 25175, *Actinobacillus viscosus* ATCC 15987, and/or *Bacteriodes fragilis* ATCC 25285.

The present invention also provides a composition according to any of the above, having an MBC of less than 0.005 mg/mL against *Streptococcus mutans* ATCC 25175, *Actinobacillus viscosus* ATCC 15987, and/or *Bacteriodes fragilis* ATCC 25285.

The present invention also provides a composition according to any of the above, having an MBC of less than 0.0025 mg/mL against *Streptococcus mutans* ATCC 25175, *Actinobacillus viscosus* ATCC 15987, and/or *Bacteriodes fragilis* ATCC 25285.

The present invention also provides a composition according to any of the above, where the composition may be made according to the process of: Dispersing and swelling polyvinylpyrrolidone in propylene glycol to obtain a first gel. Dissolving the poloxamer in heated propylene glycol to obtain a first solution. Adding the cationic biocide and any optionally included adjuvants to the first solution and thoroughly mixing to form a second solution. Adding a first part of the fumed silica to the second solution and homogenizing to obtain a second gel. Mixing the first gel and the second gel to obtain a first paste. Adding a second part of the fumed silica to the first paste and mixing to obtain a second paste. Dispersing a micronized peroxide source powder evenly into the second paste to obtain an oral composition.

DETAILED DESCRIPTION OF THE INVENTION

It should be understood that the detailed description and specific examples, while indicating the preferred embodiment of the invention, are intended for purposes of illustration only and are not intended to limit the scope of the invention.

Unless otherwise indicated, the terms "%" or "percent" when used in connection with an ingredient of the oral compositions of the invention are intended to refer to the percent by weight of the indicated ingredient in the composition.

The term "biofilm" refers to the diverse microbial community (predominantly bacteria) found on the tooth surface, embedded in a matrix of polymers of bacterial and salivary origin. Biofilm may be used synonymously with dental plaque in the description of the invention.

The present invention provides an oral care composition. The composition may be administered to the substrate of enamel, dentin, cementum, restorative metals, alloys, composites, plastics, porcelains, medical implant materials and devices of prosthodontics and orthodontics, to remove or disrupt oral biofilm or to reduce or inhibit the formation of oral biofilm. The composition may also be administered to an oral cavity to prevent or treat a condition caused by oral biofilm formation in the oral cavity, wherein the condition is selected from dental plaque, tooth decay, periodontal disease, gingivitis or halitosis.

The present invention provides an oral care composition having a cationic biocide, a peroxide source, and a stabilizing matrix. Without intending to be bound by any particular theory, it is believed that the cationic biocide and the peroxide source work synergistically, to provide an enhanced activity against oral biofilms and/or the bacteria within them. The stabilizing matrix provides a system for keeping the cationic biocide and the peroxide source shelf stable.

In accordance with the invention, the oral composition contains a cationic biocide. A suitable cationic biocide may be selected from a dual chain quaternary ammonium biocide and a single chain quaternary ammonium biocide. In some such embodiments, suitable dual chain quaternary ammonium biocides may include, for example, N, N-Didecyl-N-methyl-poly(oxyethyl) ammonium propionate, N,N-Didecyl-N,N-dimethylammonium carbonate, N,N-di-n-decyl-N,N-dimethyl-ammonium N-acetylatedal alanine carboxylate, Proline, 5-oxo-, ion(1-), N-decyl-N,N-dimethyl-1-decanaminium (1:1). (PODA), 1-Decanaminium, N-decyl-N, N-dimethyl-, salt with N-acetylalanine (1:1), Didoctyl Dimethyl Ammonium Chloride, Didoctyl Dimethyl Ammonium bromide, Ethylene-Di(Octadecyl Dimethyl Ammonium Chloride), Dioctadecyl decamethylethylene diammonium bromide, and Dioctadecyl decamethylethylene diammonium chloride. In other embodiments, suitable single chain cationic biocides may include, for example, N-Cocoyl-L-Arginineethylester DL-Pyrrolidonecarboxylate, Hexadecelpyridinium chloride, Benzyldodecyldimethyl ammonium bromide, Benzyldodecyldimethyl ammonium chloride, Dodecyl trimethyl ammonium chloride, Dodecyl Trimethyl ammonium bromide, Tetradecylpyridinium chloride, N-tetradecyl-4-ethylpyridinium chloride, Cetyltrimethyl ammonium chloride, and Cetyltrimethyl ammonium bromide. Other suitable cationic biocides or combinations of cationic biocides, however, may be used. The cationic biocide (or combination of cationic biocides) is generally present in the oral composition in amounts that range from about 0.05% to about 2.0%, optionally from 0.1% to 1.0%, from 0.05% to 0.2%, optionally from 0.05% to 0.1%, or optionally about 0.05%, 0.1%, 0.15%, or 0.2%, based on the weight of the composition.

In accordance with the invention, the oral composition contains a peroxide source. In some embodiments, the composition of present invention can include any of a variety of peroxide sources or hydrogen peroxide source, e.g., urea peroxide (carbamide peroxide) or hydrogen peroxide polymer complexes such as hydrogen peroxide-polyvinyl pyrrolidone polymer complexes (cross-linked PVP/$H_2O_2$ complex); percarbonates, perborates, or a peroxide salt, such as calcium peroxide, strontium peroxide, barium peroxide, and the like. In certain embodiments, the peroxide source may be carbamide peroxide. In other embodiments, the peroxide source may be hydrogen peroxide. In some embodiments, a combination of peroxide sources may be used. In general, the peroxide source is present in the oral composition in amounts ranging from about 0.1% to about 2.0%. However, smaller amounts and larger amounts may be used, for example, the composition may optionally contain a peroxide source in amounts from about 0.05% to about 3%. Optionally, the peroxide source may be present in the oral composition in amounts from 0.1% to 1.0%, optionally from 0.8% to 1.2%, further optionally about 0.1%, 0.25%, 0.5%, 0.75%, 1.0%, 1.5%, or 2.0%, based on the calculated weight percent as if the peroxide source were hydrogen peroxide. Thus, to calculate the weight percent of a peroxide source as used herein, one would multiply the weight percent of the peroxide source by the ratio of the molecular weight of hydrogen peroxide over the molecular weight of the peroxide source. In the case of carbamide peroxide, for example, which has a molecular weight of 94.07 g/mol, one would multiply the weight percent of the carbamide peroxide by 34.0147 over 94.07 (or about 0.362). Thus, an oral composition of the invention having 2.76% carbamide peroxide, would have the equivalent of 1% hydrogen peroxide.

As noted, the oral composition of the invention contains a stabilizing matrix. The stabilizing matrix serves to maintain the stability of one or more of the active ingredients of cationic biocide and/or the peroxide source in the composition. The stabilizing matrix generally comprises the bulk of the composition and, as such, may comprise about 80% to about 99% of the composition, optionally from 85% to 97%, further optionally from 90% to 98%, or further optionally about 94%, 95%, 96%, 97%, 98%, 99%, based on the weight of the composition.

In certain embodiments, the oral composition may be stable for at least 6 months. In other embodiments, the oral composition may be stable for at least 1 year. A stable oral composition of the invention will be substantially free visible of bubble formation resulting from the degradation of the peroxide source at the end of the specified period of time, when stored at room temperature. A stable oral composition of the invention that contains 0.002% brilliant blue (E133) will similarly be substantially free of visible loss in color over the specified time when stored at room temperature.

The stabilizing matrix comprises a carrier, a thickening system, and may optionally include compatible adjuvants. The carrier provides a medium, which may dissolve, suspend, or carry the other components of the composition. For example, the carrier can provide a medium for solubilization, suspension, and/or for forming an equilibrium mixture. The carrier can also function to deliver and/or dissolve the active ingredients of the invention on an object. To this end, the carrier may contain any orally compatible component or components that can facilitate these functions.

Generally, the carrier makes up a large portion of the composition of the invention and may be the balance of the composition apart from the thickening agents, cationic biocide, peroxide source, adjuvants, and the like. The carrier is generally a polyhydric alcohol, such as propylene glycol. The polyhydric alcohol is generally present in amounts ranging from about 40% to about 90%, from 40% to 65%, further optionally from 50% to 85%, further optionally from 60% to 87%, or further optionally from about 75% to about 85%, based on the weight of the composition.

The stabilizing matrix contains a thickening system. In general, thickening agents generally considered orally-acceptable include carboxyvinyl polymers, carbomers (polymers of acrylic acid-bonded allyl sucrose or pentaerythritol allyl ether), carrageenan, cellulosic polymers such as hydroxyl ethyl cellulose, carboxymethyl cellulose (CMC) and salts thereof (e.g., CMC sodium), natural gums such as karaya, xanthan gum, and colloidal magnesium aluminum silicate, and mixtures of the same.

However, due to the special characteristics of the invention, most of the above-mentioned thickening agents are not usable for composition of the current invention. Some would decompose the peroxide source rendering the system unstable; some would decrease the efficacy of cationic biocide due to their anionic nature, and most of the cellulose-derived thickeners are not soluble in the carrier of the composition. Some thickening agents, such as carbomers, natural gums such as karaya, xanthan gum, carrageenan, etc., may be soluble in propylene glycol, but are not suitable because of their anionic nature.

Thickening agents suitable for the thickening system of the oral composition include polyvinylpyrrolidone and/or fumed silicon dioxide, such as hydrophilic fumed silicon dioxide. These thickening agents enable the oral composition to be stable and also thicken the composition so that it can be extruded by a user from a container, such as a tube, so as to enable the composition to be used as a toothpaste or gel, and so that it can be readily manufactured.

In some embodiments, the polyvinylpyrrolidone may be present in amounts ranging from about 1% to about 6.0%, based on the weight of the composition, optionally from 2% to 5%, optionally from 2.5% to 4%, optionally about 2%, 2.5%, 3%, 4%, or 5%, based on the weight of the composition.

In some embodiments, the fumed silicon dioxide is hydrophilic fumed silicon dioxide. In some embodiments, the fumed silicon dioxide may be present in amounts ranging from about 4% to about 11%, optionally from 6% to 10%, optionally about 6%, 7%, 8%, 9%, or 10%, based on the weight of the composition.

Decomposition of the peroxide may be induced by the presence of various ingredients and trace ions within the ingredients. As such, impurities in any ingredients may impact the stability of peroxide in the system, particularly the presence of metal ions. The known tolerance level for un-stabilized peroxide in the presence of Al (III), Sn(IIIV), Zn(II), Fe(III), Cu(II), and Cr(II) metal ions is presented in Table 1.

TABLE 1

| Peroxide Tolerance level to Metal Ions | | |
|---|---|---|
| Metal ion | Amount added (ppm) | Oxygen lost % (24 hr, 100 C.)* |
| Al (III) | 10 | 2 |
| Sn(IIIV) | 10 | 2 |
| Zn(II) | 10 | 10 |
| Fe(III) | 10 | 15 |
| Cu(II) | 0.01 | 24 |
| Cr(II) | 0.1 | 96 |

*Hydrogen peroxide not stabilized.

Consequently, hydrophilic fumed silicone dioxide with a very low level of metal ions is preferred. The same is true for the other component ingredients of the invention. Inclusion of chelating agents, such as glycine, citric acid, acetic acid, ethylene diamine tetraacetic acid (EDTA), The oral care composition typically is a single-phase composition, for example a dentifrice; for example toothpaste. For the purposes of maintaining the stability of the composition, the composition preferably contains less than 3%, less than 2%, less than 1% water as an added ingredient. Typically, the present invention is free or essentially free of added water beyond that which might be naturally present in the other components of the composition. Optionally, the composition of the invention may be an anhydrous or essentially anhydrous system.

As noted, the stabilizing matrix may optionally contain adjuvants, which are compatible with each other and compatible with cationic biocide and peroxide source. Typical categories of adjuvants include a fluoride source, foaming agents, sweetening agents, flavorings, coloring agents, chelating agents, antioxidants, and the like.

However, many materials commonly used in oral care composition, such as, tartar control agents e.g., phosphates and polyphosphates (for example pyrophosphates); anti-calculus agents, e.g., tetrasodium pyrophosphate (TSPP) and sodium tripolyphosphate (STPP); natural calcium carbonate (NCC), precipitate calcium carbonate (PCC), are not compatible with the system, due to their incompatibility with the cationic biocide or the peroxide sources utilized in the invention.

In certain embodiments, the compositions of the invention optionally comprise a compatible anti-caries agent, such as an effective amount of fluoride, or a fluoride ion source. A wide variety of fluoride ion-yielding materials can be employed. Typical fluoride ion sources used in toothpastes include, but are not limited to, stannous fluoride, sodium fluoride, and sodium monofluorophosphate. However, it was determined that sodium monofluorophosphate is not compatible with the system of the composition. Typically, in those embodiments containing a source of fluoride ion, the choice of the fluoride source will be sodium fluoride.

In those embodiments have a fluoride ion source as an adjuvant, the fluoride ion is generally present in amounts ranging from about 0.001% to 1.5% based on the weight of the composition, further optionally from 0.1% to 0.15%, further optionally from 0.05% to 0.1%, based on the weight of the composition. The specific weight of the fluoride salt or salts utilized to provide the appropriate level of fluoride ion will vary based on the weight of the counter ion in the salt.

As noted, one or more compatible foaming agents may optionally be included as an adjuvant. Sodium lauryl sulfate (SLS) and sodium laureth sulfate (SLES) are both widely used in oral care products. (The other name for sodium lauryl sulfate is sodium dodecyl sulfate (SDS); usually called K12 in the dental industry.) The main use for SLS and SLES in toothpaste or oral care products is as a foaming agent to create lather, which gives an impression of cleaning power. However, SLS and SLES can irritate oral mucosa, eyes, skin, and lungs, especially with long-term use. SLES may also be contaminated with a substance called 1,4-dioxane, which is known to cause cancer in laboratory animals. This contamination occurs during the manufacturing process. Many health care products with sulfates are tested on animals to measure the level of irritation to people's skin, lungs, and eyes. For this reason, many oppose using consumer products that contain SLS and SLES. For people with an allergic constitution, sulfates may cause oral mucosal shedding and other problems. With the concern of irritation and potential adverse health effects, many people are going sulfate-free. Moreover, SLS was determined to be incompatible with the system of the invention.

In looking for a safe and compatible substitute foaming agent, various compounds were evaluated in either water or propylene glycol. The foaming agents tested included: Coconut oil acid diethanolamine, Cocamidopropylbetaine, Fatty alcohol polyoxyethylene ether, Sodium myristyl glutamate, N-Cocoyl-L-glutamic acid monotriethanolamine (Amisoft CT-12S), Sodium dodecyl sulfate, Lauryl glucoside, and Polyoxyethylene ether. The results are displayed in Tables 2 and 3. It was determined that fatty alcohol polyoxyethylene ether and poloxamer are compatible with the system of the invention.

Poloxamers are nonionic tri-block copolymers composed of a central hydrophobic chain of polyoxypropylene (poly-propylene oxide) flanked by two hydrophilic chains of polyoxyethylene, poly (ethylene oxide). Poloxamers are commonly used in industrial applications, cosmetics, and pharmaceuticals as emulsifier. As a substitute foaming agent, poloxamer proved to be a safe and efficient foaming agent that is also compatible with the system of the invention.

One or more compatible foaming agents, such as fatty alcohol polyoxyethylene ether or a poloxamer (such as Poloxamer 188 or Poloxamer 407) or mixtures thereof may be present in amounts ranging from about 0.5% to about 4%, from about 1.0% to about 3%, or from about 2% to about 3% in various embodiments, based on the weight of the composition.

The compositions of the invention may optionally comprise one or more orally-acceptable antioxidants as an adjuvant. Any antioxidant that is orally-acceptable and compatible with the system of the invention, may be used e.g., butylated hydroxyanisole (BHA), butylated hydroxytoluene (BHT), ascorbic acid, herbal antioxidants, and mixtures thereof. In some embodiments, one or more antioxidants may be present in amounts ranging of from 0.01% to 0.03% based on the weight of the composition.

As noted, the compositions of the invention may optionally comprise one or more flavoring agents as an adjuvant. Any flavoring that is orally-acceptable and compatible with the system of the invention, may be used. Experiment discovered that the commonly used oil soluble peppermint is not compatible with the system. However, water soluble peppermint is compatible with the system, as are other common flavoring agents such as menthol. In some embodiments, one or more flavoring agents may be present in amounts ranging from 0.5% to 3.0%; or from 0.8% to 1.6%, optionally from to 0.6% to 0.8%, or optionally about 0.5%, 1.0%, 1.5%, 2.0%, or 2.5%, based on the weight of the composition.

The compositions of the invention may optionally contain one or more coloring agents as an adjuvant. Any coloring agent that is orally-acceptable and compatible with the system of the invention. In some embodiments, one or more coloring agents may be present in amounts ranging from 0.001% to 0.1%, based on the weight of the composition.

The compositions of the invention may also optionally contain one or more compatible sweetening agents as an adjuvant. Any sweetening agent that is orally-acceptable and compatible with the system may be used. For example, sucralose and sodium saccharin, and combinations thereof, are compatible with the invention and may be present in amounts ranging from about 0.1% to about 2.0%, depending on the desired flavor profile for the composition.

The compositions of the invention may optionally contain one or more chelating agents as an adjuvant, such as citric acid, acetic acid, ethylene diamine tetraacetic acid, or a mixture of two or more thereof. Chelating agents may be useful for binding to free metal ions, thereby help to prevent decomposition of the peroxide and to increase the stability and shelf life of the composition. In some embodiments, one or more chelating agents are present in amounts ranging from about 0.01% to about 0.1%, based on the weight of the composition.

System Stability Evaluation

A wide variety of orally-used ingredients were evaluated for their compatibility with a peroxide source, including: Cocamidopropyl betaine (CAB 97), Fatty Alcohol Polyoxyethylene Ether 9 (AEO 9), Sodium Myristyl Glutamate, N-Cocoyl-L-glutamic acid monotri-ethanolamine (Amisoft: Amisoft CT-12S), Sodium Dodecyl Sulfate, Lauryl glucoside, Acetylated di-starch phosphate, Guar hydroxylpropyltrimonium chloride, Cationic pre-gelatinized starch, Hydrated SiO2 ZD 115, Hydrated SiO2 ZD165, Laponite XLG (lithium magnesium silicate, a synthetic clay), Carboxyvinyl polymers, Fatty alcohol polyoxyethylene ether (Polyox WSR), Glycerin, Polyvinylpyrrolidone, Carboxymethyl cellulose, Sodium carboxymethyl cellulose, Sodium tripolyphosphate (STPP), Tetrasodium pyrophosphate (TSPP), Sucralose, Fumed silica, Water soluble peppermint (Fermenich, APL0504), 1-Hexadecylpyridinium Chloride, Calcium carbonate, Calcium pyrophosphate, Sorbitol, Sodium monofluorophosphate, Sodium pyrophosphate, Sodium fluoride, Precipitate calcium carbonate, Sodium saccharin, Disodium EDTA, Menthol, Oil soluble peppermint (Firmenich, F89P961), Poloxamer188, and Poloxamer 407. The results are displayed in Tables 2 and 3.

A 0.002% solution of Brilliant Blue (E133) in propylene glycol or DI water as a baseline indicator of possible hydrogen peroxide activation was made. 20 mL of the propylene glycol color solution of was placed in a clear glass jar as a negative control for the propylene glycol group; 20 mL of the aqueous color solution was placed in a clear glass jar as a negative control for the water group. The remaining propylene glycol and DI water color solutions had carbamide peroxide added, to make 2.76% (equivalent to 1% $H_2O_2$) carbamide peroxide solutions. 20 mL of each solution with carbamide was put in a clear glass jar as positive controls separately.

Each test compound was put into two clear glass jars with 20 mL of the above polypropylene glycol/Brilliant Blue/carbamide peroxide and the DI water/Brilliant Blue/carbamide solutions. Any color dissipation over time (lightening of the color) meant that carbamide peroxide in the solution was activated and decomposition had occurred. An oxidation process occurs when the peroxide is activated thereby breaking the bonds of chromospheres, which leads to color dissipation or clearing. Compounds that resulted in color clearing were determined to have poor stabilizing effect and deemed incompatible with the system.

The results of the evaluation are displayed in Table 2 and Table 3. The negative control, positive control, and test jars were sealed, kept at room temperature and kept away from light. After 60 days, if the color was entirely dissipated, the compound was deemed to be incompatible with peroxide or the system. If there was no color dissipation or only slight dissipation, the compound was deemed compatible with the peroxide source and the system. If there was obvious color dissipation, the compound was deemed still potentially compatible with the system if suitably stabilized.

Color fading grades: no color dissipation (++++); slightly dissipation (+++); obvious dissipation (++); totally dissipated (+).

TABLE 2

Stability Test in Aqueous System
(2.76% Carbamide Peroxide in Water (equals to 1% $H_2O_2$))

| Compound | Amount | Color | Compound | Amount | Color |
| --- | --- | --- | --- | --- | --- |
| Positive control | | + | Negative control | | ++++ |
| Guar hydroxypropyl-trimonium chloride | 1% | + | Sodium Dodecyl Sulfate | 1% | + |
| Cationic pre-gelatinized starch | 1% | + | Cocamidopropyl betaine | 2% | ++++ |
| Polyquaternium-4 | 1% | + | Fatty Alcohol Polyoxyethylene Ether 9 | 2% | +++ |
| Hydrated $SiO_2$ | 10% | + | Natural calcium carbonate | 15% | + |
| Glycerin | 20% | + | Sodium acid pyrophosphate | 1% | ++ |
| Carboxymethyl cellulose | 1% | + | Sucrose fatty acid ester | 1% | + |
| Sodium carboxymethyl cellulose | 1% | + | Sorbitol | 60% | + |
| Laponite XLG | 2% | + | Sodium monofluorophosphate | 0.1% | + |
| Amisoft CT-12S | 1% | + | Calcium pyrophosphate | 10% | + |
| Lauryl glucoside | 2% | + | Sodium fluoride | 0.1% | ++ |
| Sodium tripolyphosphate | 5% | + | Precipitate calcium carbonate | 15% | + |
| Tetrasodium pyrophosphate | 5% | + | Sodium saccharin | 0.5% | ++ |
| Sucralose | 0.5% | ++ | Disodium EDTA | 0.1% | +++ |
| Fumed silica | 5% | +++ | Menthol | 0.1% | +++ |
| Acetylated di-starch phosphate | 1% | + | Poloxamer 188 | 2% | +++ |
| Water soluble Peppermint (Fermenich, APL 0504) | 1% | +++ | Premium peppermint (Firmenich, F89P961) | 1% | + |
| Hexadecyl-pyridinium Chloride | 0.1% | + | Poloxamer 407 | 2% | ++ |
| PODA | 0.1% | + | Polyvinyl-pyrrolidone PVP cross-linked | 3% | ++ |
| Chlorhexydine | 0.1% | + | $H_2O_2$ | | ++++ |

Laponite XLG: lithium magnesium silicate, synthetic clay
PODA: Proline, 5-oxo-, ion(1-), N-decyl-N,N-dimethyl-l-decanaminium (1:1).
Amisoft CT-12S: N-Cocoyl -L-glutamic acid monotriethanolamine

TABLE 3

Stability Test in Propylene Glycol
2.76% Carbamide peroxide in propylene glycol (equals to 1% $H_2O_2$)

| Compound | Amount | Color | Compound | Amount | Color |
| --- | --- | --- | --- | --- | --- |
| Positive control | | +++ | Negative control | | ++++ |
| Guar hydroxypropyl-trimonium chloride | 1% | + | Sodium Dodecyl Sulfate | 1% | + |
| Cationic pre-gelatinized starch | 1% | + | Cocamidopropyl betaine | 2% | ++++ |
| Polyquaternium-4 | 1% | + | Fatty alcohol polyoxyethylene ether | 2% | +++ |
| Hydrated $SiO_2$ ZD115 | 10% | + | Natural calcium carbonate | 15% | + |
| Glycerin | 20% | ++ | Sodium acid pyrophosphate | 1% | ++ |
| Carboxymethyl cellulose | 2% | + | Sucrose fatty acid ester | 1% | + |
| Sodium carboxymethyl cellulose | 1% | + | Sorbitol | 60% | + |
| Laponite XLG | 2% | + | Sodium monofluorophosphate | 0.1% | + |
| Amisoft CT-125 | 1% | + | Calcium pyrophosphate | 10% | + |
| Lauryl glucoside | 2% | + | Sodium fluoride | 0.1% | +++ |
| Sodium tripolyphosphate | 5% | + | Precipitate calcium carbonate | 15% | + |
| Tetrasodium pyrophosphate | 5% | + | Sodium saccharin | 0.5% | +++ |
| Sucralose | 0.5% | +++ | Disodium EDTA | 0.1% | +++ |
| Fumed silica | 5% | +++ | Menthol | 0.1% | +++ |
| Acetylated di-starch phosphate | 1% | + | Poloxamer 188 | 2% | ++ |
| Water soluble peppermint (Firmenich, APL0504) | 1% | +++ | Premium peppermint (Firmenich, F89P961) | 1% | + |
| Hexadecyl-pyridinium Chloride | 0.1% | ++ | Poloxamer 407 | 2% | ++ |
| PODA | 0.1% | ++ | Polyvinyl-pyrrolidone PVP Cross-linked | 3% | +++ |
| Chlorhexydine | 0.1% | ++ | $H_2O_2$ | 3% | ++++ |

Laponite XLG: lithium magnesium silicate, synthetic clay
PODA: Proline, 5-oxo-, ion(1-), N-decyl-N,N-dimethyl-l-decanaminium (1:1).
Amisoft CT-12S: N-Cocoyl -L-glutamic acid monotriethanolamine Results of testing demonstrated that many commonly used ingredients for dentifrice would activate the peroxide and make the system unstable, such as: Hydrated $SiO_2$, Sodium tripolyphosphate (STPP), Tetrasodium pyrophosphate (TSPP), Precipitate calcium carbonate, Natural calcium carbonate, Calcium pyrophosphate, Sorbitol, Sodium Dodecyl Sulfate, Colloidal silica, Sodium monofluorophosphate, Sorbitol, Glycerin, Sodium carboxymethyl cellulose, Carboxymethyl cellulose, etc. Any peroxide-containing formulation would not be stable with any of the above ingredients in the system.

System Stability Evaluation:

To assess the stability of some prior art peroxide-containing dentifrices, the following experiments were performed:

U.S. Pat. No. 9,999,585 describes an oral care composition comprising (i) a whitening complex comprising cross-linked polyvinylpyrrolidone complexed with hydrogen peroxide, and (ii) a hydrogen peroxide stabilizing agent comprising clay comprising a sodium lithium magnesium silicate.

U.S. Pat. No. 10,052,270 describes an oral care composition comprising (i) a peroxide whitening agent comprising a whitening complex of cross-linked polyvinylpyrrolidone complexed with hydrogen peroxide, (ii) sodium acid pyrophosphate ($Na_2H_2P_2O_7$) in an amount of from 0.1 wt % to 3 wt % based on the weight of the composition, and (iii) less than 3 wt. % water based on the weight of the composition; and further comprising at least one humectant; wherein the at least one humectant comprises propylene glycol and glycerin, and wherein the composition comprises propylene glycol and glycerin in an amount of from 25 wt. % to 60 wt. % based on the weight of the composition; and further comprising 1 to 2 wt. % tetrasodium pyrophosphate as an tartar control agent.

Two compositions were prepared according to U.S. Pat. No. 9,999,585 (formulations 585a and 585b) and two compositions were prepared according to U.S. Pat. No. 10,052,270 (formulations 270a and 270b), as set out in Table 4 below. The stability of formulations using cross-linked PVP/$H_2O_2$ complex (585a and 270a) or carbamide peroxide (585b and 270b) as peroxide sources were evaluated in the compositions.

TABLE 4

Prior Art Compositions Tested for Stability

|  | 585a | 270a | 585b | 270b |
|---|---|---|---|---|
| Fumed silica | — | 1.5 | — | 1.5 |
| 85% syrupy phosphoric acid | 0.2 | 0.2 | 0.2 | 0.2 |
| PEG 600 | 3 | 10 | 3 | 10 |
| Pluracare L1220F | 7.5 | 10 | 7.5 | 10 |
| Glycerin | 23.61 | 5 | 23.61 | 5 |
| Propylene glycol | 28 | 25 | 28 | 25 |
| Sodium lithium magnesium silicate | 2 | — | 2 | — |
| Cross-linked PVP | 2 | 2 | 2 | 2 |
| Cross-linked PVP/$H_2O_2$ complex | 11 | 5.5 | 0.0 | 0.0 |
| Carbamide peroxide | 0.0 | 0.0 | 3.0 | 3.0 |
| Sodium saccharin | 0.6 | 0.6 | 0.6 | 0.6 |
| Sodium monofluorophosphate | 0.76 | 0.76 | 0.76 | 0.76 |

TABLE 4-continued

Prior Art Compositions Tested for Stability

|  | 585a | 270a | 585b | 270b |
|---|---|---|---|---|
| Tetrasodium pyrophosphate (TSPP) | 2 | 2 | 2 | 2 |
| Butylated hydroxytoluene (BHT) | 0.03 | 0.03 | 0.03 | 0.03 |
| Sodium lauryl sulfate (SLS) | 2 | 2 | 2 | 2 |
| Calcium pyrophosphate | 15 | 35.11 | 15 | 35.11 |
| Sodium acid pyrophosphate | — | 1.0 | — | 1.0 |
| Brilliant Blue (E133) | 0.002 | 0.002 | 0.002 | 0.002 |

Test samples 585a, 585b and test samples 272a, 272 b were placed in sealed clear glass jars at room temperature and kept away from light. After 24 hours, the color of formulations 585a, 585b, and 272a had disappeared. The paste became colorless and many bubbles appeared in the paste. The color of formulation 272b had minor dissipation with a few bubbles. After 3 days, the color of formulation 272b disappeared as well. The paste became colorless and many bubbles appeared.

With sodium acid pyrophosphate ($Na_2H_2P_2O_7$) as peroxide stabilizer (formulations 270a and 279b), the composition was not stable with either Cross-linked PVP/$H_2O_2$ complex or carbamide peroxide as a peroxide source.

With sodium lithium magnesium silicate (Laponite XLG) as peroxide stabilizer (formulations 585a and 585b), the system was not stable with either Cross-linked PVP/$H_2O_2$ complex or carbamide peroxide as a peroxide source.

A composition according to U.S. Pat. No. 9,999,585 (claim 27) was also prepared for the stability evaluation.

TABLE 5

Prior Art Formulation with Sodium Lithium Magnesium Silicate

| Composition | W/W |
|---|---|
| Sodium lithium magnesium silicate (Laponite XLG) | 2 |
| Cross-linked polyvinylpyrrolidone | 2 |
| Glycerin | 30 |
| Propylene glycol | 30.5 |
| Pluracare L1220F | 7.5 |
| Polyethylene glycol 600 | 3 |
| Cross-linked PVP/$H_2O_2$ complex | 10 |
| Calcium pyrophosphate | 15 |
| Brilliant Blue (E133) | 0.002 |

The above composition was prepared and placed in sealed clear glass jars at room temperature, and kept away from light. After 3 days, the blue paste became colorless and many bubbles appeared in the paste.

With sodium lithium magnesium silicate (Laponite XLG) as a peroxide stabilizer, the system was not stable with Cross-linked PVP/$H_2O_2$ complex as a peroxide source.

EXAMPLE 1

Example Formulations

Several compositions of the invention are illustrated in the following non-limiting examples (Table 6). Each example composition comprises the following ingredients, each being based on the weight of the composition.

TABLE 6

| Ingredient | Formulations | | | | | | |
|---|---|---|---|---|---|---|---|
| | 1 | 2 | 3 | 4 | 5 | 6 | 7 |
| Proline, 5-oxo-, ion(1-), N-decyl-N,N-dimethyl-l-decanaminium | 0.10 | 0 | 0.05 | — | 0.10 | — | 0.20 |
| Polyvinylpyrrolidone | 2.00 | 2.00 | 5.00 | 2.50 | 2.50 | 4.00 | 2.00 |
| Fumed $SiO_2$ | 9.00 | 9.00 | 5.00 | 8.00 | 10.00 | 7.00 | 9.00 |
| Carbamide peroxide | 2.86 | 2.86 | 5.72 | 5.72 | 0.29 | 1.43 | 2.86 |
| Hexadecylpyridinium Chloride | — | 0.10 | — | 0.05 | — | 0.20 | — |
| Menthol | 0.10 | 0.10 | 0.05 | 0.05 | — | 0.10 | 0.01 |
| Sodium fluoride | 0.10 | 0.05 | 0.10 | — | — | — | — |
| Water soluble Peppermint | 1.00 | 1.00 | 1.50 | 1.00 | — | 1.00 | 2.00 |
| Sucralose | 0.60 | — | 0.50 | — | — | — | 0.70 |
| Saccharin sodium | — | 0.60 | — | 0.50 | — | 0.70 | — |
| Paloxamer 188 | 3.00 | — | 3.00 | — | — | — | — |
| Fatty Alcohol Polyoxyethylene Ether 9 | — | 3.00 | — | 3.00 | — | 3.00 | 3.00 |
| Brilliant Blue (E133) | 0.002 | 0.002 | 0.002 | 0.002 | 0.002 | 0.002 | — |
| Propylene glycol | qs 100 | qs 100 | qs 100 | qs 100 | qs 100 | qs 100 | qs 100 |

It is understood that when formulations are described, they may be described in terms of their ingredients, as is common in the art, notwithstanding that these ingredients may react with one another in the actual formulation as it is made, stored and used, and such products are intended to be covered by the formulations described.

EXAMPLE 2

Process for Mixing the Composition

The procedures for preparation of the composition:
a. Polyvinylpyrrolidone is dispersed in propylene glycol to let the polyvinylpyrrolidone totally swell, to obtain Gel A;
b. Poloxamer is dissolved in heated propylene glycol (45° C.) to obtain Solution B;
c. The cationic biocide and adjuvants are added to solution B, thoroughly mixed at room temperature to obtain Solution C;
d. The fumed silica is divided into three parts. One third of the fumed silica is added to solution C, homogenized and then a second part of fumed silica is added, then homogenized, to obtain Gel B;
e. Gel A and Gel B are thoroughly mixed, to obtain a homogeneous paste A;
f. The last part of the fumed silica is added to the paste A and thoroughly homogenized to obtain paste B.
g. The micronized peroxide source powder is then dispersed evenly to the above paste B, to obtain the final product.
h. Discharge batch.

All the mixing occurs between about 24° C. to 29° C., preferably room temperature.

EXAMPLE 3

Stability Testing

Several toothpastes of varying compositions were prepared and tested for stability using indicators outlined previously.
Sample 1 (Example 1, formulation 1), Sample 2 (Example 1, formulation 3), Sample 3 (Example 1, formulation 5), and Sample 4 ((Example 1, formulation 2) were prepared according to the procedures of Example 2.

Sample 1, Sample 2, Sample 3 and Sample 4 were prepared and put in sealed clear glass jars at room temperature and kept away from light. Color dissipation and bubble generation were used as indicators of the hydrogen peroxide decomposition. Any lightening of color or bubble generation meant carbamide peroxide in the paste was activated and decomposition had occurred indicating instability.

After 6 months, no color change or bubble generation was observed, thereby confirming the stability of the composition of the invention.

The Sample 1, Sample 2 and Sample 3 were used for tests in Example 4, Example 5 and Example 6.

EXAMPLE 4

MIC and MBC of the Composition Against *S. mutans* and *A. viscosus*

Agar Dilution method recommended by National Committee for Clinical Laboratory Standards (NCCLs) were used to determine the minimum inhibitory concentration (MIC) and minimum bactericidal concentration (MBC) of *Streptococcus mutans* and *Actinobacillus viscosus*, the main bacteria in oral biofilm and the most important pathogenic bacteria for dental caries and periodontal diseases.

Test sample and the bacteria strains:
1. Test sample: Example 1, formulation 5 (stored 6 month before test)
2. *Streptococcus mutans* (ATCC 25175)
3. *Actinobacillus viscosus* (ATCC 15987)
4. *Bacteriodes fragilis* (ATCC 25285) (for quality control)

Procedures:
1. The test sample was vortex mixed with DI water to make serial diluted slurry solutions at: 1/10, 1/20, 1/40, 1/80, 1/160, and 1/320 concentrations.
2. 50 mL of each of each serially diluted slurry was centrifuged for 15 min. at 15000 rpm. at room temperature. The supernatant was kept for use.
3. 1 mL of each of the above supernatant was mixed with 9 mL BHI sterilized agar, and prepared in agar plates. The concentration in the agar plates was 1/100, 1/200, 1/400. 1/800, 1/1600, and 1/3200 respectively.
4. Resuscitation and purification of the testing strains was conducted according conventional culture method for anaerobic bacteria. Cultured for 48 hours, medium:

BHI-S (XOID, England); anaerobic tank: DY-II (YiWu) with 80% N2+10% CO2+10% H2. The pure cultures were inoculated into BHI medium and cultured under the same conditions for 48 hours; with the bacterial concentration of 48-hour cultures adjusted to 0.5 McFarland ($1.5 \times 10^8$ cells/mL).

5. MIC and MBC determination: 48 hour cultures ($1.5 \times 10^8$ cells/mL) were inoculated with a bacterial multipoint plater (SAKUMA, Japan) to the agar plates with different sample concentrations; cultured 48 hrs. in an anaerobic tank with 80% N2+10% CO2+10% H2. The MIC and MBC values were then recorded.

6. Results: The MIC and MBC of the test sample are shown in Table 7.

TABLE 7

MIC and MBC for *S. mutans* and *A. viscosus*

|     | Streptococcus mutans | Actinobacillus viscosus | Bacteriodes fragilis (control strain) |
| --- | --- | --- | --- |
| MIC | 1/800 | 1/800 | 1/800 |
| MBC | 1/400 | 1/400 | 1/400 |

The MIC and MBC for *Streptococcus mutans* (ATCC 25175) was 1/800 and 1/400, respectively. Similarly, the MIC and MBC for *Actinobacillus viscosus* (ATCC 15987) was also 1/800 and 1/400 respectively. For comparison, a 2016 publication determined that amongst the dentifrices tested (Colgate® Total®, Colgate® Cavity Protection®, Crest® Pro-Health®, and Crest® Pro-Health Clinical®)), Colgate® Total®, containing 0.3% trislocan, had the lowest MBC against streptomyces under anaerobic conditions, with an MBC of 3.1-5.2 mg/ml and an MIC against total oral anaerobes of about 1.5 mg/mL. (Forbes et al., Simultaneous Assessment of Acidogenesis Mitigation and Specific Bacterial Growth Inhibition by Dentifrices, PLoS One. 2016; 11(2): e0149390). This represents an MIC and MBC that is three orders of magnitude higher than the dentifrice of the present invention, which demonstrated MBC and MIC values of around 0.0025 mg/mL and 0.00125 mg/mL, respectively. Without intending to be bound by any particular theory, it is believed that there is a synergism between the cationic biocide and the peroxide that enhances the antibacterial activity in the formulations of the present invention.

EXAMPLE 5

Existing Biofilm Disruption

Twenty (10 pairs) of freshly extracted first upper premolars from orthodontic patients were used for the study. Right after removal from the mouth, the teeth were rinsed with saline, and the crown was stained with Ci plaque indicator (Ci Medical CO, Ltd.) to disclose existing biofilms. The teeth were rinsed with saline and photos were taken of the labial, distal, mesial and lingual surfaces of each tooth. The stained area was then measured according to the index classification to determine biofilm index.

A 1.5 g sample of toothpaste (Example 1, composition 1, sample stored for 6 month before test) was vortex mixed with 8.5 g deionized water for 3 min to make a sample solution (solution S). Deionized water was used for a comparative solution (solution C). One tooth from a pair of stained teeth from the same patient was randomly immersed in each solution (one tooth from the pair in solution S; one tooth from the pair in solution C). The specimens were void of any mechanical disturbance. There were 10 teeth in the sample group and 10 teeth in the comparative group. The teeth in solution S were designated as T1 to T10; the teeth in solution C were designated as C1 to C10. The pair of teeth were removed from solution S and solution C, respectively, rinsed with saline, stained, and the biofilm index was recorded for the four sides of each tooth at 10 min., 20 min., and 40 min. intervals.

Results:

Calculate the mean index value of labial, distal, mesial and lingual surface index readings of each tooth. Use the mean index value as the index of the tooth at each time interval.

TABLE 8

Biofilm Index Change after Toothpaste Treatment

| Test pair | 0 min. | 10 min. | 20 min. | 30 min. | 40 min. |
| --- | --- | --- | --- | --- | --- |
| T 1 | 3.5 | 2.5 | 2.5 | 2.5 | 2.5 |
| C 1 | 3.5 | 3.5 | 3.5 | 3.5 | 3.5 |
| T 2 | 4 | 3.5 | 3.25 | 3.25 | 3.25 |
| C 2 | 4 | 4 | 4 | 4 | 4 |
| T 3 | 4.5 | 3.75 | 3.5 | 3.5 | 3.25 |
| C 3 | 4.25 | 4.25 | 4.25 | 4.25 | 4.25 |
| T 4 | 3.25 | 3 | 2.75 | 2.5 | 2.25 |
| C 4 | 3.25 | 3.25 | 3.25 | 3.25 | 3.25 |
| T 5 | 3.5 | 3.25 | 3.25 | 3.25 | 3 |
| C 5 | 3.5 | 3.5 | 3.5 | 3.5 | 3.5 |
| T 6 | 3.75 | 3.5 | 3.25 | 3.25 | 3.25 |
| C 6 | 3.75 | 3.75 | 3.75 | 3.75 | 3.75 |
| T 7 | 3.75 | 3.25 | 3.25 | 3.25 | 2.75 |
| C 7 | 3.25 | 3.25 | 3.25 | 3.25 | 3.25 |
| T 8 | 4 | 3 | 2.5 | 2.5 | 2.5 |
| C 8 | 4 | 4 | 4 | 4 | 4 |
| T 9 | 4 | 3.75 | 3.75 | 3.75 | 3.75 |
| C 9 | 4 | 4 | 4 | 4 | 4 |
| T 10 | 4.25 | 4.25 | 4.25 | 4.25 | 4.0 |
| C 10 | 4.25 | 4.25 | 4.25 | 4.25 | 4.25 |

Biofilm index grading: 0 = no stain on the tooth surface; 1 = scattered stain at gingival margin; 2 = stain covering the gingival margin is less than 1 mm; 3 = stain covering the gingival margin is over 1 mm but less than 1/3 of the tooth surface; 4 = stain covering 1/3-2/3 of the tooth surface; 5 = stain covering 2/3 of the tooth surface.

In the sample group, after 40 min. treatment, the biofilm was reduced by 21%. There were no changes in the comparative group. Conclusion: The sample toothpaste demonstrated a capacity to reduce/disrupt existing biofilm on human teeth.

EXAMPLE 6

Artificial Biofilm Disruption

Twenty-four bovine permanent central incisors were cut to obtain 24 labial enamel specimens approximately 10 $mm^2$. The enamel specimens were embedded in an autopolymerizing methacrylate resin in such a manner that only the enamel surfaces were exposed. The specimens were embedded with the aid of a mold so as to facilitate the positioning of the specimens in a V-White brushing machine. The enamel surfaces were rubbed with 600 grit silicon carbide sand paper under constant flow water. Surfaces were then polished with a dental polishing paste. Specimens were then lightly etched. This etching procedure consisted of a 60-second immersion in 0.12N (1%) hydrochloric acid, followed by a 30-second immersion in a super-saturated solution of sodium carbonate to expedite stain accumulation and adherence. A final etch was performed with 1% phytic acid for 60 seconds. The specimens were then rinsed and ultrasonically cleaned in deionized water. After air-drying, the specimens were treated in a staining/bacteria broth. The staining/bacteria broth consisted of 2.7 g of finely ground instant coffee, 2.7 g of finely-ground instant tea, and 2.0 g of finely-ground gastric mucin dissolved into 800 ml of sterilized trypticase soy broth. Twenty-six ml of a 24-hour Sarcocyst (Sarcina lutea turtox) culture was also added to the staining broth.

The specimens were immersed in the staining/bacteria broth in a staining container and the container was then placed in an incubator (37° C.) with the specimens remaining immersed in the staining/bacteria broth. The staining/bacteria broth was replaced twice daily, for seven consecutive days. With each broth change, the specimens were rinsed with deionized water to remove any loose deposits. After the seven-day staining period, a darkly stained film was apparent on the enamel surfaces. The specimens were removed from the staining container, rinsed well, allowed to air dry for about ten minutes, and then refrigerated until use.

Each specimen was scanned with a 3 Shape Trios intraoral scanner (Denmark) to determine the L* value. The specimens were divided into two groups; one test group and one comparative group. Each specimen was given a numerical number from 1-24 and evenly divided into Sample group and Comparative group according to their L* readings. Each group had 12 specimens and the Sample and Comparative groups were balanced to include specimens with similar L* values. The Sample group had teeth T1, T2, T3, T4, T5, T6, T7, T9, T10, T12, T13, T14; and the Comparative group had teeth T8, T11, T15, T16, T17, T18, T19, T20, T21, T22, T23, T24.

A computer color matching (CCM) system of the body color of 29 shade tabs from a VITAPAN 3D-Master shade guide was used to match the specimen readings from the 3 Shape-Trio readings. The 29 shades of the VITA shade guide 3-D values are: 0M1, OM2, OM3, 1M1, 1M2, 2L1.5, 2L2.5, 2M1, 2M2, 2M3, 2R1.5, 2R2.5, 3L1.5, 3L2.5, 3M1, 3M2, 3M3, 3R1.5, 3R2.5, 4L1.5, 4L2.5, 4M1, 4M2, 4M3, 4R1.5, 4R2.5, 5M1, 5M2, 5M3. They are arranged from brightest color to darkest color.

The 3 Shape Trios intraoral scanner's color readings were three-dimensional values. For comparison, the 29 3-D readings of VITA shade guide were represented by numerical color grade from 1 to 29. In Table 9, 1 represents the brightest color (0M1) and 29 represent the darkest color (5M3) correspondingly.

3-D readings are arranged from lightest color (0M1) to darkest color (5M3); the corresponding numbers also represent the colors from lightest (1) to darkest (29).

The tooth specimens were mounted onto the V-White cross brushing machine equipped with a soft nylon-filament (Oral B soft toothbrush) and adjusted a tension of 150 g upon the enamel surface.

Sample group: Sample toothpaste (Example 1, formulation 3, stored for 6 month before test) was made into slurry consisting of 25 g of toothpaste mixed with 50 mL of de-ionized water.

Comparative group: An ADA reference material was used as a comparison tooth surface cleaning reference. The reference comparison slurry consisted of 10 g ADA standard Calcium pyrophosphate mixed with 50 mL of a mixture of 0.5% carboxymethyl cellulose and 10% glycerin in water.

The specimens of the Sample group were brushed with the slurry of the sample toothpaste and the specimens of the Comparative group were brushed with slurry of ADA Calcium pyrophosphate. At each brushing cycle, the specimens were brushed for 800 double strokes per min. for three min. with the corresponding slurry (the Sample toothpaste slurry or the ADA Calcium pyrophosphate slurry). The slurries were replaced with new slurry at each of the 3 min intervals. A total of 14 cycles were run.

A computer color matching (CCM) system of 29 shade tabs from the VITAPAN 3D-Master shade guide was used to match the specimen readings from the 3 Shape-Trio readings of the 24 specimens. The 29 shades of the VITA shade guide 3-D values are: 0M1, OM2, OM3, 1M1, 1M2, 2L1.5, 2L2.5, 2M1, 2M2, 2M3, 2R1.5, 2R2.5, 3L1.5, 3L2.5, 3M1, 3M2, 3M3, 3R1.5, 3R2.5, 4L1.5, 4L2.5, 4M1, 4M2, 4M3, 4R1.5, 4R2.5, 5M1, 5M2, 5M3. They are arranged from brightest color to darkest color.

The before and after color readings of the sample group are displayed in Table 10.

TABLE 9

Three-D Readings vs. Color Grades

| 3-D reading | 0M1 | 0M2 | 0M3 | 1M1 | 1M2 | 2L1.5 | 2L2.5 | 2M1 | 2M2 | 2M3 |
|---|---|---|---|---|---|---|---|---|---|---|
| Color grade | 1 | 2 | 3 | 4 | 5 | 6 | 7 | 8 | 9 | 10 |
| 3-D reading | 2R1.5 | 2R2.5 | 3L1.5 | 3L2.5 | 3M1 | 3M2 | 3M3 | 3R1.5 | 3R2.5 | 4L1.5 |
| Color grade | 11 | 12 | 13 | 14 | 15 | 16 | 17 | 18 | 19 | 20 |
| 3-D reading | 4L2.5 | 4M1 | 4M2 | 4M3 | 4R1.5 | 4R2.5 | 5M1 | 5M2 | 5M3 | |
| Color grade | 21 | 22 | 23 | 24 | 25 | 26 | 27 | 28 | 29 | |

TABLE 10

Sample Group Color Readings Before and After

|  | T1 | T2 | T3 | T4 | T5 | T6 | T7 | T9 | T10 | T12 | T13 | T14 |
|---|---|---|---|---|---|---|---|---|---|---|---|---|
| bef. 3D | 5M2 | 5M2 | 5M2 | 5M1 | 5M2 | 5M2 | 5M1 | 5M3 | 5M1 | 5M1 | 5M3 | 5M1 |
| aft. 3D | 1M2 | 2M1 | 1M2 | 1M1 | 1M1 | 1M2 | 1M1 | 2M1 | 1M1 | 1M2 | 2M1 | 0M2 |
| bef. L* | 59.48 | 59.48 | 59.48 | 58.55 | 59.48 | 59.48 | 58.55 | 60.51 | 58.55 | 58.55 | 60.51 | 58.55 |
| aft. L* | 78.43 | 72.94 | 78.43 | 76.48 | 76.48 | 78.43 | 76.48 | 72.94 | 76.48 | 78.43 | 72.94 | 79.59 |
| bef. N | 28 | 28 | 28 | 27 | 28 | 28 | 27 | 29 | 27 | 27 | 29 | 27 |
| aft. N | 5 | 8 | 5 | 4 | 4 | 5 | 4 | 8 | 4 | 5 | 8 | 2 |

3D: three-dimensional value;
L*: L* value;
N: numerical color grade

The before and after color readings of the comparative group are displayed in Table 11.

TABLE 11

Comparative Group Color Readings Before and After

|  | T8 | T11 | T15 | T16 | T17 | T18 | T19 | T20 | T21 | T22 | T23 | T24 |
|---|---|---|---|---|---|---|---|---|---|---|---|---|
| bef. 3D | 5M2 | 5M2 | 5M2 | 5M2 | 5M1 | 5M1 | 5M2 | 5M2 | 5M1 | 5M1 | 5M1 | 5M3 |
| aft. 3D | 5M2 | 5M1 | 4M2 | 5M2 | 4M1 | 5M1 | 5M1 | 5M1 | 5M1 | 4M1 | 5M1 | 5M1 |
| bef. L* | 59.48 | 59.48 | 59.48 | 59.48 | 58.55 | 58.55 | 59.48 | 59.48 | 58.55 | 58.55 | 58.55 | 60.51 |
| aft. L* | 59.48 | 58.55 | 64.16 | 59.48 | 64.22 | 58.55 | 58.55 | 58.55 | 58.55 | 64.22 | 58.55 | 58.55 |
| bef. N | 28 | 28 | 28 | 28 | 27 | 27 | 28 | 28 | 27 | 27 | 27 | 29 |
| aft. N | 28 | 27 | 23 | 28 | 22 | 27 | 27 | 27 | 27 | 22 | 27 | 27 |

3D: three-dimensional value;
L*: L* value;
N: numerical color grade

Paired t-Tests were performed to evaluate the results. Statistical analysis data is displayed in Table 12.

TABLE 12

Paired t-Tests

| | Paired Differences | | | | | | | |
|---|---|---|---|---|---|---|---|---|
| | | | | 95% Confidence interval of difference | | | | 2-tailed Signi- |
| | mean | Std. deviation | Std. Error mean | Lower | Upper | t | df | ficance |
| Pair 1 S bef. vs. C bef. | 0.086 | 0.648 | 0.187 | −0.326 | 0.498 | 0.495 | 11 | 0.655 |
| Pair 2 S bef. vs. S aft. | −17.240 | 2.384 | 0.688 | −18.755 | −15.725 | −25.048 | 11 | 0.000 |
| Pair 3 C bef. vs. C aft. | −0.939 | 2.527 | 0.730 | −2.545 | 0.667 | −1.287 | 11 | 0.224 |
| Pair 4 S aft. vs. C aft. | 16.387 | 3.917 | 1.131 | 13.898 | 18.875 | 14.494 | 11 | 0.000 |

S: Sample group;
C: Comparative group;
bef.: before test;
aft.: after test.

Results from paired t-test showed:

The colors of the test group and the comparative group had no difference prior to the tests (P>0.05), which meant the Sample groups were comparable.

The before and after color differences for the Sample groups were statistically significant (P<0.05), which meant the Sample composition was effective in reducing biofilm.

The before and after color differences for the Comparative group were statistically significant (P<0.05), which meant the abrasive force of the ADA Calcium pyrophosphate slurry was also effective for reducing biofilm.

However, the significant differences in color change (P<0.05) between the Sample group and the Comparative group clearly demonstrated the superior efficacy of the Sample composition.

What is claimed is:

1. An oral care product consisting of a peroxide source, a cationic biocide, and a non-aqueous matrix, said non-aqueous matrix consisting of propylene glycol, fumed silica, and polyvinylpyrrolidone, said non-aqueous matrix optionally further consisting of one or more orally-acceptable compatible ingredient selected from the group consisting of anti-caries agent, foaming agent, sweetening agent, flavoring agent, coloring agent, chelating agent, and antioxidant, where each optional ingredient is compatible with any other optional ingredient, the peroxide source, and the cationic biocide, such that the non-aqueous matrix stabilizes the peroxide source and maintains the efficacy of the cationic biocide, and wherein the range of the weight ratio of propylene glycol, fumed silica and polyvinylpyrrolidone is: 1: 0.03-0.15: 0.01-0.08.

2. The oral care product according to claim 1, wherein the cationic biocide is a quaternary ammonium salt or a biguanide.

3. The oral care product according to claim 1, wherein the cationic biocide is Proline, 5-oxo-, ion (1-), N-decyl-N, N-dimethyl-1-decanaminium or cetyl pyridinium chloride.

4. The oral care product according to claim 1, wherein the peroxide source is selected from the group consisting of urea peroxide, calcium peroxide, hydrogen peroxide, sodium percarbonate, sodium perborate and polyvinylpyrrolidone-$H_2O_2$ complexes.

5. The oral care product according to claim 1, wherein the oral care product for removing an oral biofilm.

6. The oral care product according to claim 5, wherein the product for removing oral biofilm is a paste.

7. The oral care product according to claim 6, wherein the oral care product has a foaming agent in the paste that is polyethylene/polypropylene glycol copolymer (poloxamer) or Primary Alcohol Ethoxylate.

8. The oral care product according to claim 6, wherein the paste contains one or more compatible ingredients selected from the group consisting of coloring agent, sweetener, flavoring agent, antioxidant, foaming agent, chelating agent, and fluoride.

9. The oral care product according to claim 6, wherein the paste is a toothpaste, which is made according the following procedures:
   a) disperse the polyvinylpyrrolidone in propylene glycol to obtain a gel A;
   b) dissolve poloxamer in heated propylene glycol to obtain a solution B;
   c) add the cationic biocide and one or more excipients selected from the group consisting of sweetener, coloring agent, antioxidant, chelating agent, flavoring essence to solution B that has been allowed to cool, then mix well to obtain a solution C;
   d) add two thirds of the fumed silica into solution C and mix well to obtain gel B;
   e) mix gel A and gel B to obtain a non-aqueous paste A;
   f) add one third of the fumed silica to the non-aqueous paste A and mix well to obtain a non-aqueous paste B;
   g) add a pulverized peroxide source to the non-aqueous paste B and thoroughly disperse to obtain the final product.

10. An oral care product according to claim 1, having a compatible ingredient selected from the group consisting of cocamidopropyl betaine, fatty alcohol polyoxyethylene ether 9, sodium acid pyrophosphate, sucralose, fumed silica, water soluble peppermint, sodium fluoride, sodium saccharin, disodium EDTA, menthol, poloxamer 188, poloxamer 407, polyvinylpyrrolidone, and glycerin.

11. An oral care product according to claim 1, where an ingredient is determined to be a compatible ingredient by the process of mixing a sample of the ingredient with a 20 ml sample of propylene glycol containing 0.002% brilliant blue (E133) and 2.76% carbamide peroxide, placing the mixture in a glass jar that is then sealed and stored at room temperature and protected from light, and then examining the mixture to determine if blue color is still evident after 6 months.

12. An oral care product according to claim 1, further including a compatible chelating agent selected from the group consisting of glycine, citric acid, acetic acid, and ethylene diamine tetraacetic acid (EDTA).

13. An oral care product according to claim 1, further including sodium fluoride as a compatible anti-caries agent.

14. An oral care product according to claim 1, further including a compatible antioxidant selected from the group consisting of butylated hydroxyanisole (BHA), butylated hydroxytoluene (BHT), ascorbic acid, herbal antioxidants, and mixtures thereof.

15. An oral care product according to claim 1, further including a compatible coloring agent.

16. An oral care product according to claim 1, having a compatible foaming agent selected from the group consisting of fatty alcohol polyoxyethylene ether, a Poloxamer, and mixtures thereof.

17. An oral care product according to claim 1, having a compatible anti-caries agent, a compatible foaming agent, a compatible sweetening agent, and a compatible flavoring agent.

18. An oral care product according to claim 17, where the anti-caries agent is sodium fluoride.

19. An oral care product according to claim 17, where the compatible foaming agent selected from the group consisting of fatty alcohol polyoxyethylene ether, a Poloxamer, and mixtures thereof.

20. An oral care product according to claim 17, where the compatible sweetening agent selected from the group consisting of sucralose, sodium saccharin, and mixtures thereof.

* * * * *